Figure 1:
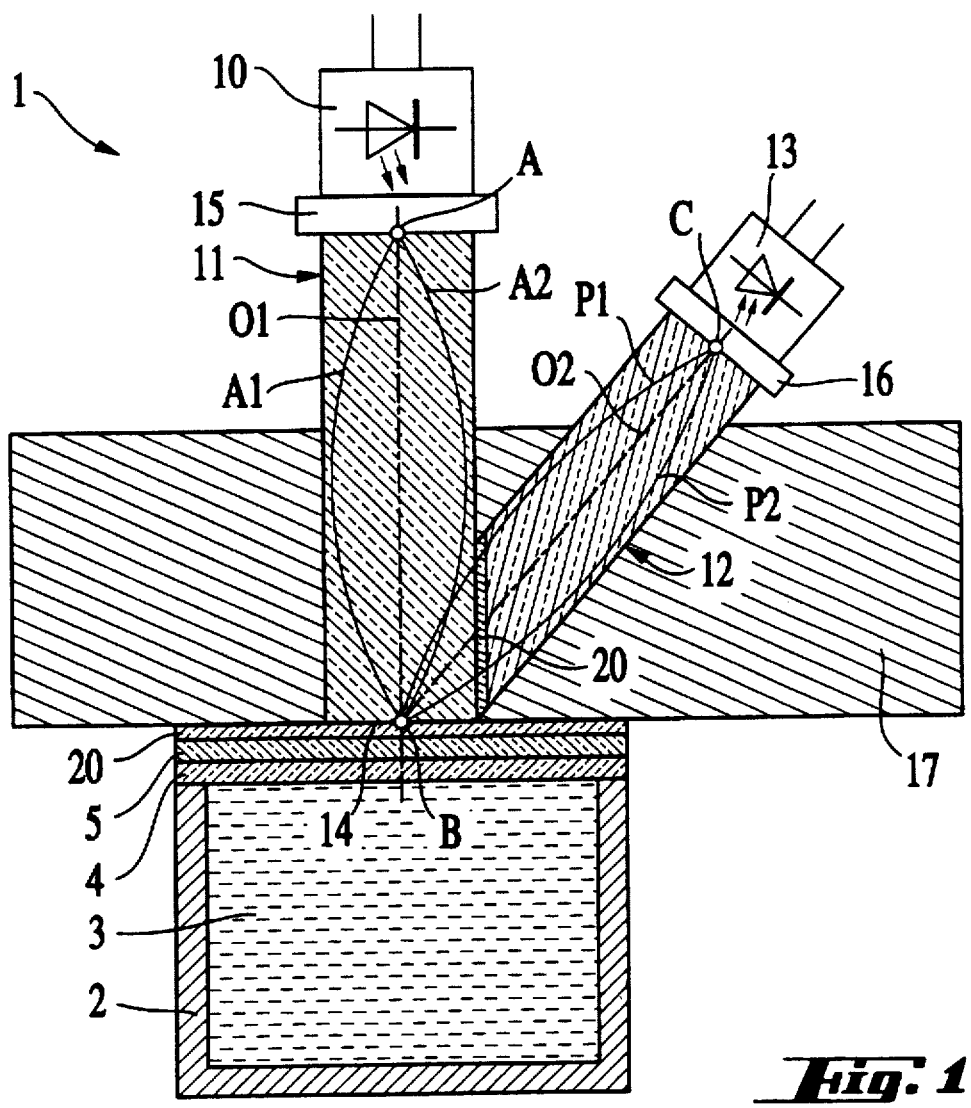

United States Patent [19]

Bruno et al.

[11] Patent Number: 5,757,014

[45] Date of Patent: May 26, 1998

[54] OPTICAL DETECTION DEVICE FOR ANALYTICAL MEASUREMENT OF CHEMICAL SUBSTANCES

[75] Inventors: Alfredo Emilio Bruno, Oberwil; Steven Mark Barnard, Basel; Marizel Rouilly, Gipf-Oberfrick, all of Switzerland

[73] Assignee: Novartis Corporation, Summit, N.J.

[21] Appl. No.: 625,330

[22] Filed: Apr. 1, 1996

[30] Foreign Application Priority Data

Apr. 7, 1995 [EP] European Pat. Off. ............ 95810234

[51] Int. Cl.[6] ................................................ G01N 21/64
[52] U.S. Cl. ........................................ 250/458.1; 356/317
[58] Field of Search ........................... 250/458.1, 461.1; 356/417, 317, 318

[56] References Cited

U.S. PATENT DOCUMENTS

| | | | |
|---|---|---|---|
| 4,853,547 | 8/1989 | Bach | 250/458.1 |
| 4,892,640 | 1/1990 | Wolfbeis et al. | 250/458.1 X |
| 5,108,932 | 4/1992 | Wolfbeis | |
| 5,128,019 | 7/1992 | Karpf et al. | |
| 5,157,262 | 10/1992 | Marsoner et al. | 250/458.1 |
| 5,304,492 | 4/1994 | Klinkhammer | |

FOREIGN PATENT DOCUMENTS

| | | |
|---|---|---|
| 0357586 | 3/1990 | European Pat. Off. |
| 0371953 | 6/1990 | European Pat. Off. |
| 616211 | 9/1994 | European Pat. Off. ............ 250/458.1 |
| 9306459 | 4/1993 | WIPO |

OTHER PUBLICATIONS

Selfoc Micro Lens —Technical Information.

A. E. Bruno et al. Trends in Analytical Chem. vol. 13 No. 5, 190–198 (1994).

*Primary Examiner*—Edward J. Glick
*Attorney, Agent, or Firm*—George R. Dohmann

[57] ABSTRACT

In the optical detection device (1), the excitation light guide (11) and the emission light guide (12) form a structural unit having the end face (14) facing the fluorescence changer (4). The end face (14) physically corresponds substantially to one of the boundary surfaces of the two light guides (11, 12). As a result, the detection device (1) can be separated in a simple manner into an optical part and a mechanical part which are in optical contact only by way of the end face (14). All of the elements in the optical light path are connected in a mechanically stable manner by means of the index-matching medium 20, as a result of which the light between the light source (10) and the photoelectric sensor (13) propagates only in media having a comparable refractive index. The light source (10) is preferably a light-emitting diode. A plurality of those detection devices can be combined to form a compact detection apparatus with which the substance (3) can be examined with regard to several constituents in one measuring operation.

19 Claims, 8 Drawing Sheets

OPTICAL DETECTION DEVICE FOR ANALYTICAL MEASUREMENT OF CHEMICAL SUBSTANCES

The invention relates to an optical detection device for analytical measurements of a substance and to a corresponding optical detection apparatus and a corresponding optical analysis apparatus for analytical measurements of chemical substances.

A large number of measuring devices for qualitative and quantitative chemical analyses of substances are known to the person skilled in the art. Specifically for the analysis of small volumes of sample, techniques based, for example, upon electrophoresis or chromatography or in which the substance is examined spectroscopically without previously being separated are used nowadays. In both cases, the detection of the constituents is very often carried out by means of optical methods and, therefore, great importance is attached to the development of new optical detection devices with a view to improving instrumentation in the analysis sector. Optical detection devices include inter alia arrangements for absorption measurements, refractive index measurements and fluorescence measurements.

The classical optical detector consists of an optical bench on which the individual components are mounted, which components usually consist of materials having widely differing physical properties (e.g. thermal expansion, refractive index, elastic constants). The sensitivity and resolution power of such systems is usually limited, therefore, by noise and drift effects caused by the thermal expansion of the materials used, vibrations and schlieren effects in the optical light path which begins at the light source and ends at the photoelectric sensor. The main sources of noise and drift are the various transitions between regions of differing optical density (hereinafter referred to as "optical transitions") where reflection and refraction phenomena occur. In addition to the scattered light, the intensity fluctuations of the light source also have an adverse effect, especially on fluorescence measurements, since the fluctuations manifest themselves both in the fluorescence light and in the background noise.

In a known arrangement for fluorescence measurements, the substance to be analysed is brought into contact with a fluorescing agent which is caused to fluoresce by an excitation light. Certain constituents of the substance, to which the fluorescing agent is sensitive, cause a change in the fluorescence light, for example with regard to its intensity, which is registered by a photoelectric sensor. Fluorescing agents having that property of changing their fluorescence light upon coming in contact with a constituent are referred to hereinafter as "fluorescence changers".

One possible method of eliminating the mentioned disadvantages of classical optical detectors is disclosed, for example, in EP-A-0 616 211. The underlying concept therein is to minimise the number of optical transitions between the light source and the photoelectric sensor. That is achieved by passing the excitation light emitted by the light source onto a capillary tube containing the substance through a special light guide that has a refractive index gradient, and passing the emission light, coming from the capillary tube, onto the photoelectric sensor through a further light guide. In all of the transition regions between the individual optical elements there is an index-matching medium having a refractive index that substantially corresponds to that of the wall material of the capillary tube. In addition, that index-matching medium connects the individual optical elements in a mechanically stable manner.

That concept has the advantage that, apart from in the interior of the capillary tube, the excitation light and the emission light always propagate in media having a substantially constant optical density. As a result, the scattered light is reduced. The mechanically stable arrangement has the advantage that vibrations do not interfere with the optical light path. Since the light guides and the capillary tubes have comparable thermal expansion coefficients and the individual elements are in thermal contact with one another through the index-matching medium, there are virtually no interference effects from thermal causes either. That procedure of forming the optical light path in such a manner that the light propagates with a minimum of refraction and reflection, and according to which the various optical elements are arranged in as mechanically stable as possible a construction and are in direct contact with one another in order to make it easier to achieve thermal equilibrium, is usually referred to in the literature as "pigtailing" (see, e.g. A. E. Bruno et al., Trends in analytical chemistry, Vol. 13, No. 5, 190 (1994)).

The problem of intensity fluctuations is solved in EP-A-0616211 by the use of light-emitting diodes (LEDs) as the light source. LEDs that are powered by stabilised voltage sources are orders of magnitude more stable with regard to light intensity than lasers or conventional light sources. They exhibit virtually no intensity fluctuations.

Optical detection apparatus of the kind described inter alia in EP-A-0 616 211 is typically employed in capillary electrophoresis (CE), in chromatography using microcolumns, in capillary chromatography and, especially, in high performance liquid chromatography (HPLC). Such apparatus, however, involves high expenditure in its manufacture. Both the excitation light guide and the emission light guide have to be dimensioned extremely accurately and each has to be exactly positioned on the capillary tube individually in order to achieve as efficient as possible an illumination of the sample and in order to optimise the intensity of the emission light meeting the photoelectric sensor.

If the substance to be examined is to be changed, the entire optical arrangement usually has to be set up again and the individual optical elements have to be re-set.

When fluorescence changers are used for the detection of constituents of a substance, photobleaching—especially at high excitation light intensities which are often desirable for sufficiently strong fluorescence—also shortens the life of such an apparatus considerably. Photobleaching is the effect where the fluorescing agent loses its fluorescence property with increasing illumination time. That effect naturally becomes apparent sooner at high excitation light intensities. Accordingly, the fluorescence changer required for the detection becomes unusable with time. In that case also, the entire optical arrangement has to be set up again and the optical elements re-set.

Such optical detection apparatus therefore has the limitation that, whenever the part containing the substance and the fluorescence changer becomes unusable, whether as a result of degradation effects or as a result of changing the substance to be examined, the entire optical part also has to be re-adapted in a laborious, time-consuming manner.

That limitation prevents such optical detection apparatus from being available in a compact, mechanically insensitive and easily handled form for, for example, mobile use in a broad field of application outside the modern analysis and research laboratory.

Proceeding from that prior art, the problem of the invention is, therefore, to provide an optical detection device that exhibits the afore-mentioned advantages of pigtailing and in which the optical elements are structurally arranged in such a manner that the part comprising the substance and the fluorescence changer can be replaced without all the optical elements having to be re-adapted and re-set. The optical detection device is to be simple and inexpensive to manufacture and assemble and is to be suitable for mobile use in a large number of applications. That device is also to be compact so that a plurality of such devices can be combined to form an optical detection apparatus with which a substance can be examined with regard to several constituents.

According to the invention, therefore, the excitation light guide is connected to the emission light guide in such a manner that the two light guides substantially form a structural unit having an end face facing the fluorescence changer. The end face physically corresponds substantially to one of the boundary surfaces of the two said light guides.

As a result of that constructional measure, the device according to the invention can typically be divided into two parts: an optical part which comprises at least the light source, the light guides and the photoelectric sensor and which is designed for permanent use, and a mechanical part which comprises at least the fluorescence changer, the sample container and the substance and which can easily be replaced. Accordingly, only the replaceable part has to be replaced, when necessary, by another part in such a way that the excitation light leaving the end face meets the fluorescence changer at least partially. Additional manipulation of the optical part is no longer necessary upon replacement. The device according to the invention is therefore especially suitable for economical mass-production, since the replaceable part can be designed, for example, to be used only once. As a result, there are also no problems with photobleaching.

A further advantage of the device according to the invention is that the optical part can be produced in a higher quality, since it is usable repeatedly independently of the replaceable part and therefore has a longer life.

It is especially beneficial to connect the excitation light guide and the emission light guide to form a structural unit by means of an index-matching medium since, as a result, reflections and refractions at the interface are minimal.

An especially preferred light source for the device according to the invention is a light-emitting diode (LED) which, powered by a stabilised voltage source, provides distinctly more stable light intensities than do other customary light sources. That solves the problem of intensity fluctuations of the excitation light, which is a considerable one for fluorescence measurements especially.

The device according to the invention furthermore has the advantage that the fluorescence changer or the sample container needs to be optically contactable through only one face, which physically corresponds substantially to one of the boundary surfaces of the light guides, namely the common end face of the two light guides, and not through at least two as is disclosed, for example, in EP-A-0 616 211. That means an enormous saving in space, which is especially advantageous for a compact design. As a result of that compact form, it is possible to combine a plurality, and preferably six, of the optical detection devices according to the invention to form an optical detection apparatus. That apparatus according to the invention may, for example, be arranged in such a manner that all of the excitation light guides and emission light guides are located in paired receiving openings in a holding body. In addition, all of the sample containers may be formed by a common measurement chamber. Furthermore, it is possible to arrange the fluorescence changers on a common carrier element. That carrier element is then connected to the holding body in such a manner that each excitation/emission light guide is associated with a respective fluorescence changer which is met substantially only by the excitation light emerging from the end face associated with it. Since the fluorescence changers may be sensitive to various constituents of the substance held in the measurement chamber, this apparatus according to the invention offers the advantage that several constituents of the substance can be detected with it. In addition, the mechanical part, which comprises at least the fluorescence changers, the measurement chamber and the substance, can be replaced in a simple manner without its being necessary to make changes to or to re-set the optical part, which comprises at least the excitation/emission light guides, the light sources and the photoelectric sensors. The apparatus according to the invention accordingly has a compact form, is simple to use, is cheap to manufacture and is therefore suitable for mobile use in a large number of applications.

Other advantageous measures and preferred embodiments of the device according to the invention and of the apparatus according to the invention will be apparent from the dependent claims.

Figure 2:
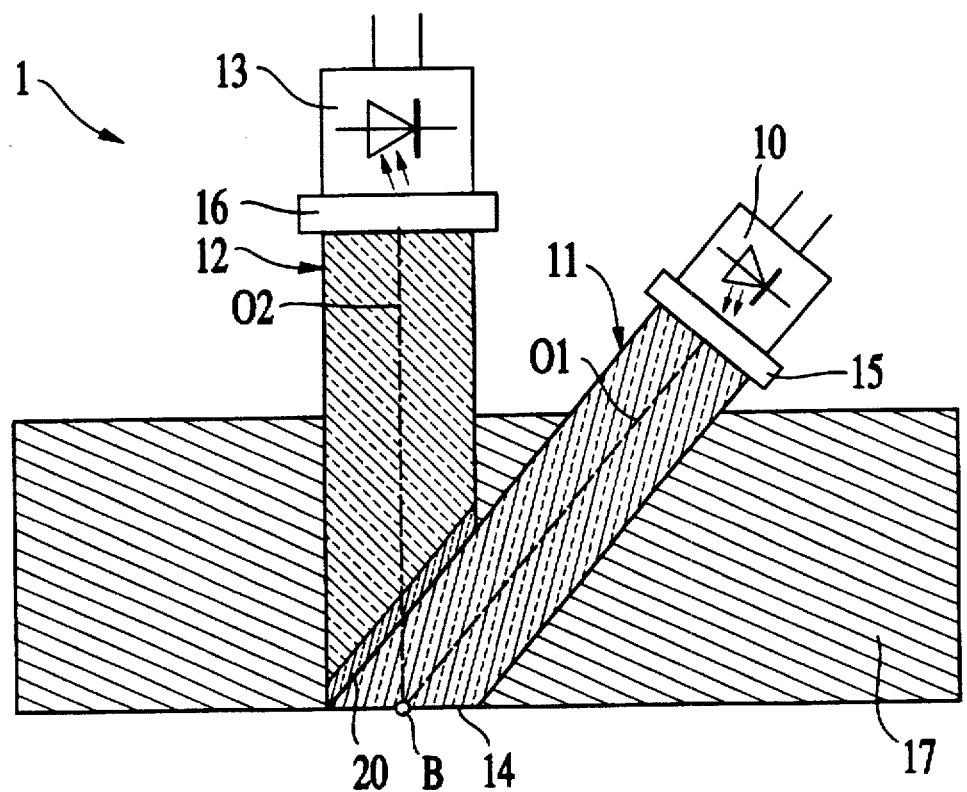
Figure 3:
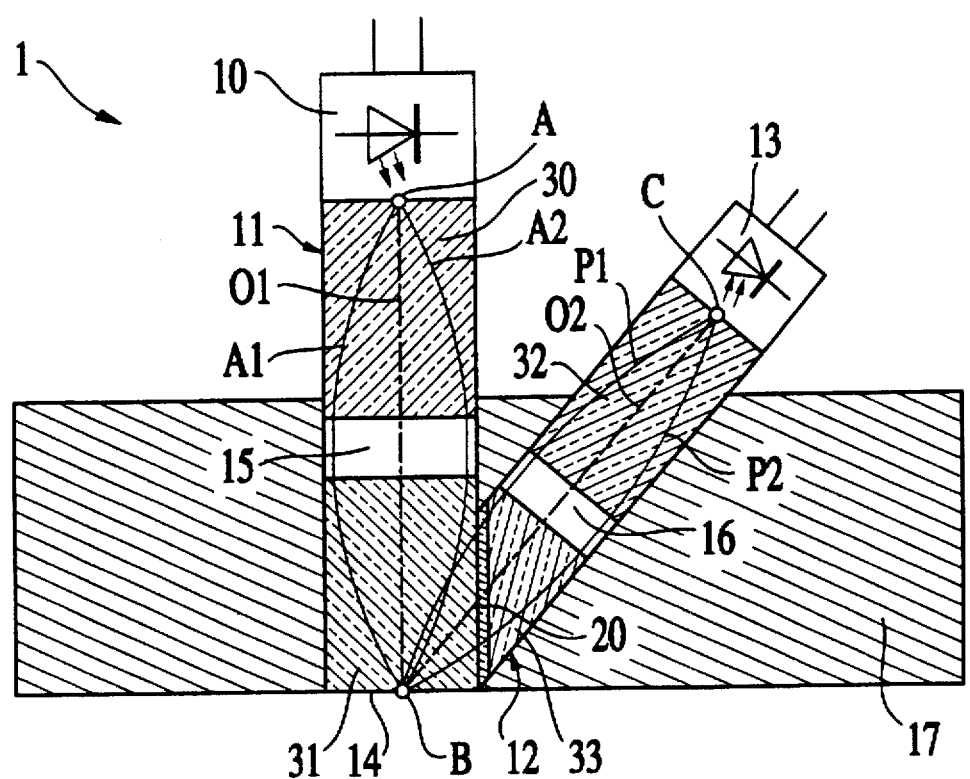
Figure 4:
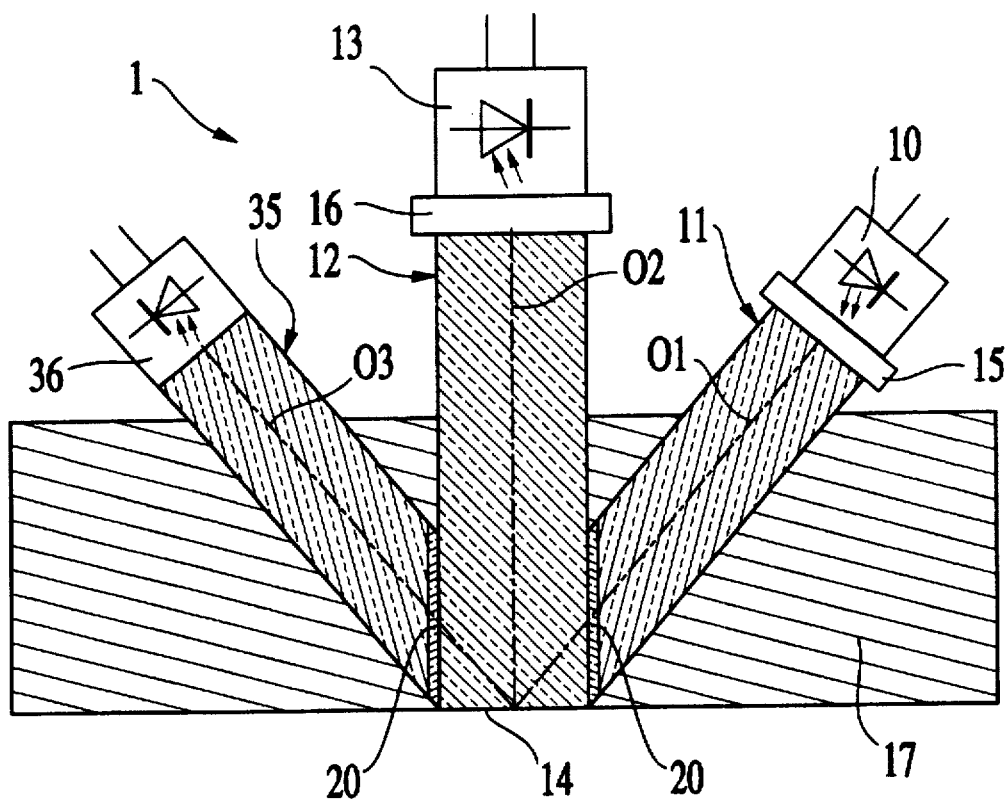
Figure 5:
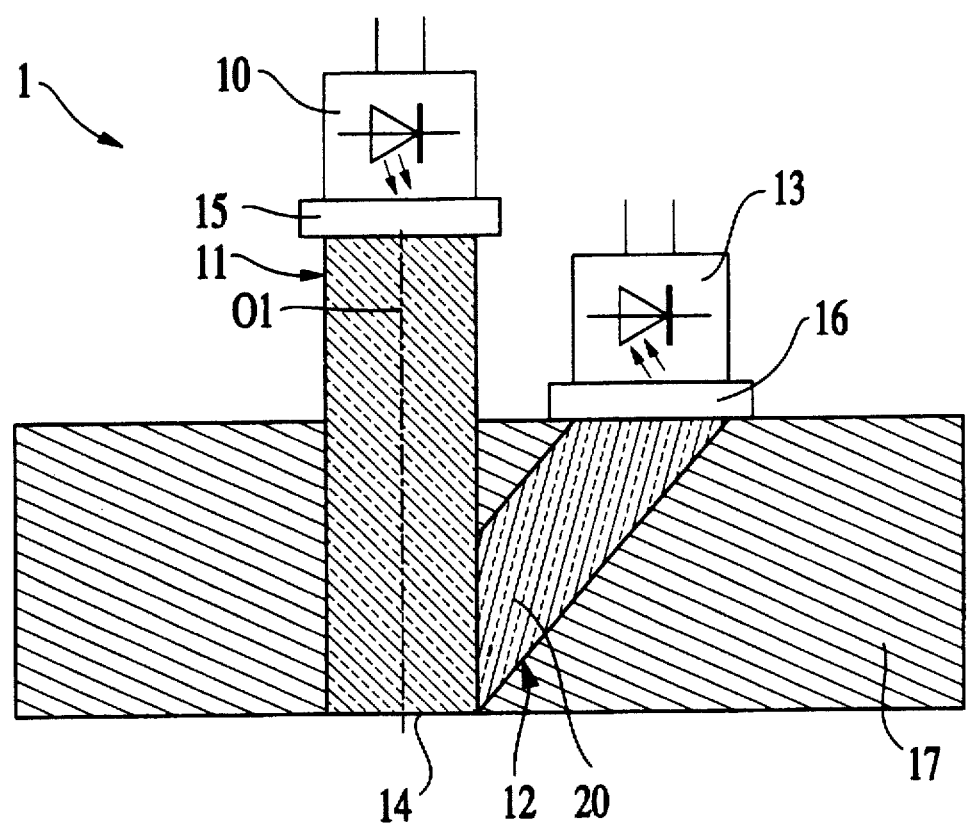
Figure 6:
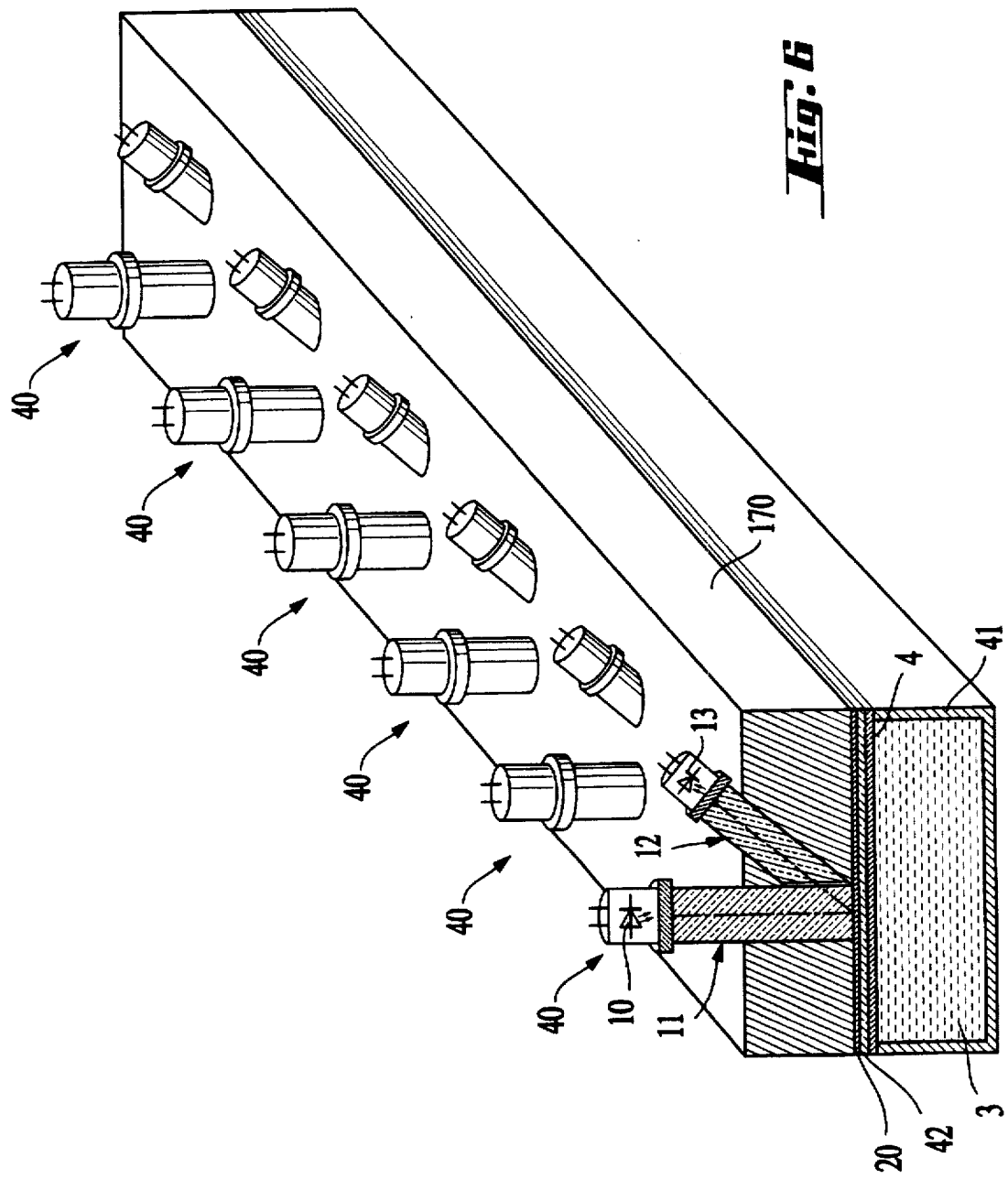
Figure 7:
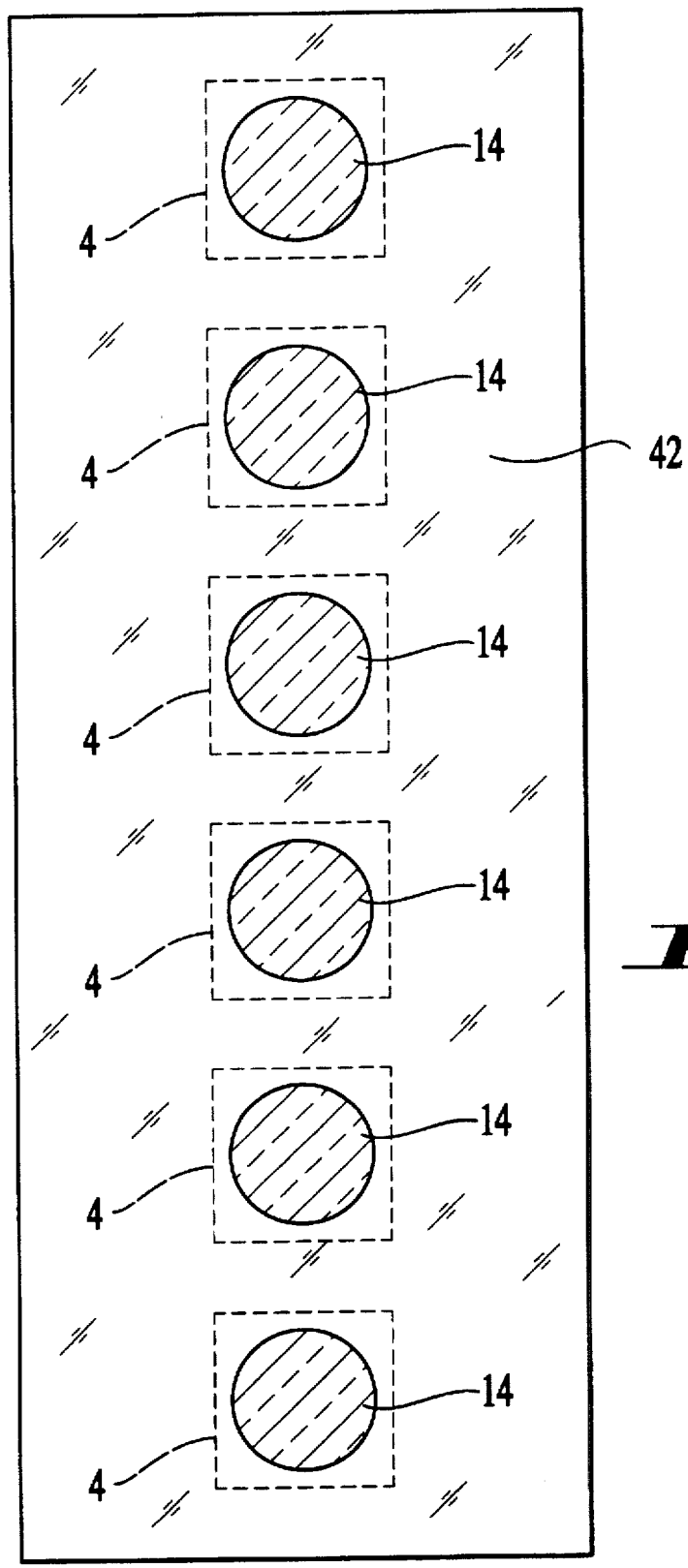
Figure 8:
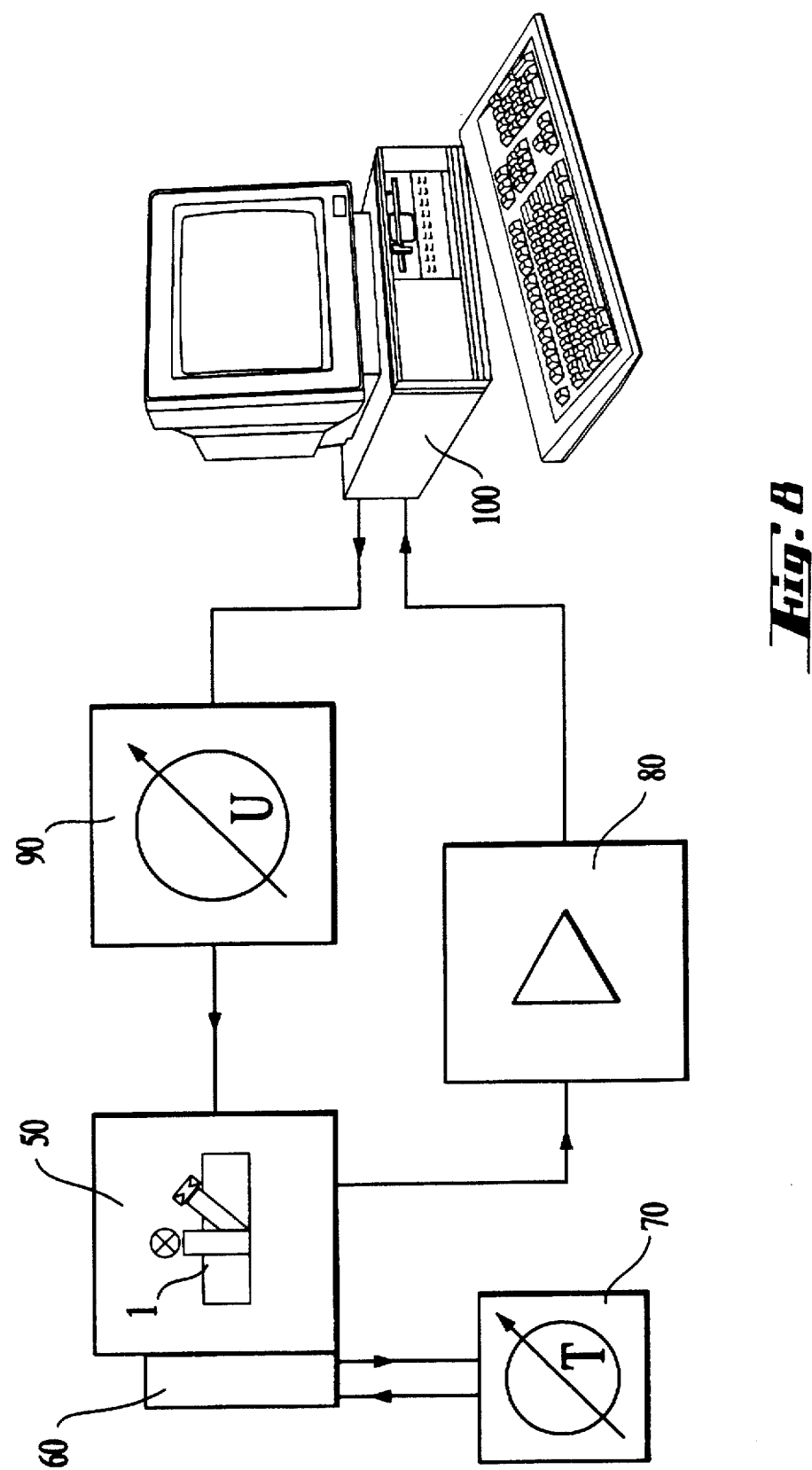

The invention is described in detail below with reference to embodiments and to the drawings. In the schematic drawings, which are not to scale:

FIG. 1 shows a section through a first embodiment of the device according to the invention, FIG. 2 shows a section through the optical part of one variant of the first embodiment of the device according to the invention, FIG. 3 shows a section through the optical part of a second embodiment of the device according to the invention, FIG. 4 shows a section through the optical part of a third embodiment of the device according to the invention, FIG. 5 shows a section through the optical part of a fourth embodiment of the device according to the invention, FIG. 6 is a view in perspective of an embodiment of the optical detection apparatus according to the invention (front side shown in section), FIG. 7 is a plan view of an embodiment of the carrier element with the fluorescence changers of the optical detection apparatus according to the invention, and FIG. 8 is a block diagram of an embodiment of the optical analysis apparatus according to the invention, which comprises an optical device according to the invention or an optical apparatus according to the invention.

In the following description of the preferred embodiments with reference to the drawings, identical or functionally equivalent parts are provided with identical reference numerals. FIG. 1 shows schematically a section through a first embodiment of the optical detection device according to the invention. The latter is designated 1 in its entirety. The device according to the invention typically comprises a sample container 2 for a substance 3, a fluorescence changer 4 which can be contacted by the substance 3, a light source 10 for emitting an excitation light, a photoelectric sensor 13, for example a photodiode, for emission light coming from the fluorescence changer 4, and two light guides, namely an excitation light guide 11 and an emission light guide 12. In the first embodiment, the two light guides 11, 12 each comprise a material in which the refractive index is not constant but exhibits a gradient substantially perpendicular to the principal direction of propagation of the light in the light guide. The principal directions of propagation of the light are determined by the optical axes O1 and O2.

The light source 10, the excitation light guide 11 and the fluorescence changer 4 are so arranged relative to one another that the excitation light emitted by the light source 10 is able to enter the excitation light guide 11 and is guided by the latter substantially in such a manner that it meets at least part of the fluorescence changer 4. The fluorescence changer 4, the emission light guide 12 and the photoelectric sensor 13 are so arranged relative to one another that at least part of the emission light coming from the fluorescence changer, substantially guided by the emission light guide 12, meets the photoelectric sensor 13.

The excitation light causes fluorescence in the fluorescence changer 4. The emission light so emitted meets the photoelectric sensor 13 and can be converted by means of the latter into an electrical signal which is then available in the usual manner for further processing and evaluation. If a specific constituent of the substance 3, to which the fluorescence changer 4 is sensitive, contacts the fluorescence changer 4, a change in the emission light, for example with regard to its intensity, results, which is registered by the photoelectric sensor 13. In that manner, it is possible to carry out analytical measurements of chemical substances.

Fluorescence changers of that kind are state of the art per se and are known to the person skilled in the art in large number. They do not, therefore, require any further explanation. In order to examine the substance 3 with regard to a specific constituent, it is necessary, of course, to select in each case a fluorescence changer that is sensitive to that specific constituent.

According to the invention, the excitation light guide 11 is connected to the emission light guide 12 in such a manner that the two light guides substantially form a structural unit having an end face 14 facing the fluorescence changer. According to the invention, that end face 14 furthermore physically corresponds substantially to one of the boundary surfaces of the two light guides 11, 12, and the end face 14 substantially forms both the optical emergence surface for the light passing from the light source 10 through the excitation light guide 11 and the optical entry surface for the emission light coming from the fluorescence changer 4. The optical emergence surface is that surface through which the excitation light meeting the fluorescence changer 4 leaves the structural unit formed by the excitation light guide 11 and the emission light guide 12. The optical emergence surface may, but does not have to, correspond to one of the boundary surfaces of the excitation light guide 11. The optical entry surface is that surface through which the emission light meeting the photoelectric sensor 13 enters the structural unit formed by the excitation light guide 11 and the emission light guide 12. The optical entry surface may, but does not have to, correspond to one of the boundary surfaces of the emission light guide 12.

It is advantageous to cement the two light guides 11, 12 together by means of an index-matching medium 20. That index-matching medium is a transparent adhesive having a refractive index that corresponds, to within substantially +/−20%, to the refractive indices of the two light guides 11, 12. Suitable adhesives are, for example, two-component adhesives such as those obtainable, for example, from the Applicant under the trade name Araldite® XW 396 and XW 397. It is especially advantageous to use as the index-matching medium a transparent adhesive that is curable by exposure to a suitable energy form, usually UV light. As a result of that measure, it is easier to carry out the final adjustment. The adhesive does not cure until—after correct positioning of the two light guides 11, 12 relative to each other—it is exposed to the suitable energy form.

In the preferred embodiment of the device according to the invention shown in FIG. 1, the excitation light guide 11 consists of an optical filter 15, the function of which is explained hereinafter, and an optical gradient index element which, especially preferably, is a GRIN lens. Such GRIN lenses are state of the art (see e.g. A. E. Bruno et al., Trends in analytical chemistry, Vol. 13, No. 5, 190 (1994)) and are obtainable, for example, under the trade name SELFOC® from NIPPON SHEET GLASS Co. Ltd. The GRIN lens is essentially a cylindrical rod with a parabolic distribution of the refractive index. The refractive index is greatest along the axis of the cylinder, which corresponds to the optical axis O1, and decreases as the perpendicular distance from the axis of the cylinder increases. The refractive index gradient ensures that light beams A1, A2 entering the lens follow a sinusoidal path in the rod. The length of those GRIN lenses is usually given in the unit "pitch". In a rod of length 1 pitch, a light beam passes through exactly one period of the sine wave. If, for example, a point source of light is located on the optical axis at one of the planar boundary surfaces of a 0.5 pitch GRIN lens, the image of the light source will be located on the opposite boundary surface, likewise on the optical axis. If, in the same arrangement, the GRIN lens is one having a length of 0.25 pitch, the light will leave the lens as parallel light. When a GRIN lens smaller in length than 0.5 pitch is used, the light of a point source located at a certain distance from the planar boundary surface of the lens will similarly be focused into a point again, which then, however, lies outside the lens.

Using GRIN lenses, therefore, the same optical imaging can be carried out according to essentially the same imaging rules as when classical spherical lenses are used, and the expressions used—such as, for example, focal point, principal plane—also correspond to those from classical geometrical optics. GRIN lenses have the great advantage, however, that being cemented to other elements does not interfere with their lens properties. That is different from classical lenses, in which the optical imaging properties rely upon refraction at the two curved boundary surfaces. GRIN lenses are therefore especially suitable for implementing the pigtailing concept.

In connection with the pigtailing concept, optical fibres are also often used. These are subject to the limitation, however, that the light emerging from the end thereof always diverges. In comparison therewith, GRIN lenses have the advantage that, with them, by suitable selection of the pitch length, the emerging light can be made either parallel or divergent or can also be focused.

The emission light guide 12 in the first embodiment, which is shown in FIG. 1, consists of a second optical filter 16, the function of which is described hereinafter, and an optical gradient index element which, especially preferably, is a GRIN lens. The two light guides 11, 12 are joined together, especially preferably cemented together by means of the index-matching medium 20, to form substantially a structural unit in such a manner that the excitation light guide 11 and the emission light guide 12 are inclined relative to each other and the principal directions of propagation of the light, determined by the optical axes O1, O2, are at an oblique angle to each other. That measure provides the advantage that the scattered light produced by reflection in the region of the fluorescence changer 4 reaches the photoelectric sensor 13 only in a greatly attenuated form. It is precisely in fluorescence measurements that the signal-to-noise ratio is quite decisively influenced by scattered light. Owing to the oblique-angled arrangement of the two light guides 11, 12 relative to each other, the excitation light meets the fluorescence changer 4 at a greater angle to the optical axis O2 of the emission light guide 12 than, for example, in the case of a parallel arrangement of the two light guides 11, 12. Consequently, the light reflected in the region of the fluorescence changer 4 is also more inclined relative to the optical axis O2 of the emission light guide 12. If, however, the angle of incidence of the light on the GRIN lens exceeds a certain limit, the light can no longer enter the lens. For that reason, the oblique-angled arrangement of the two light guides 11, 12 relative to each other reduces the intensity of the scattered light that reaches the photoelectric sensor 13.

The structural unit of excitation light guide 11 and emission light guide 12 is produced, for example, by cutting one of the two GRIN lenses of the excitation light guide 11 and the emission light guide 12 at an oblique angle to its respective optical axis O1 or O2, purely by way of example at an angle of about 45°, and then polishing the cut face. The two GRIN lenses are then cemented together by means of the index-matching medium 20.

The dimensions of the two GRIN lenses of the excitation and emission light guides 11, 12 are such that a nodal line of the structural unit formed by the two light guides 11, 12 lies substantially in the region of the fluorescence changer. The nodal line is a straight line joining a focal point of the excitation light guide 11 to a focal point of the emission light guide 12. It is especially advantageous if the nodal line is reduced to a point, that is to say if the excitation and emission light guides 11, 12 have a common focal point B.

The excitation light guide 11 furthermore comprises, in the first embodiment of the device according to the invention, the optical filter 15, which is preferably an interference filter. By means of that filter it is possible to select or to limit the wavelength(s) of the excitation light meeting the fluorescence changer 4. The emission light guide 12 comprises the second optical filter 16, which is preferably an interference filter. It serves to select or to limit the wavelength(s) of the emission light meeting the photoelectric sensor. Since, as fluorescence light, the emission light usually has a different wavelength from the excitation light which causes the fluorescence, the intensity of the undesired scattered light can be further reduced by means of the second filter 16, which has a beneficial effect on the signal-to-noise ratio.

As already explained hereinbefore, the light source 10 is especially preferably a light-emitting diode (LED) that radiates coherent or incoherent light. In the first embodiment, the light source 10 is, for example, cemented to the optical filter 15, preferably by an adhesive corresponding to the index-matching medium 20 which connects the two GRIN lenses of the excitation light guide 11 and the emission light guide 12. Before cementing, the plexiglass housing which usually surrounds the LED crystal can be removed to such an extent as to allow the optical filter to be positioned in immediate proximity to the LED crystal. The optical filter 15 is cemented to the boundary surface of the GRIN lens of the excitation light guide 11 facing it, preferably likewise by an adhesive corresponding to the index-matching medium 20. It is, however, also possible, for example, to drill a hole first in the plexiglass housing surrounding the LED crystal. The depth of that hole in the housing extends into the immediate proximity of the LED crystal so that the optical filter 15 and the GRIN lens of the excitation light guide 11 can be positioned as close as possible to the LED crystal in order to obtain as high as possible an efficiency of the excitation light. The optical filter 15 and the GRIN lens of the excitation light guide 11 are inserted into the drilled hole and joined there by an adhesive. Especially preferably, an adhesive corresponding to the index-matching medium 20 is again used here.

The connection between the second optical filter 16 and the boundary surface of the GRIN lens of the emission light guide 12 facing it, and the connection between the second optical filter 16 and the photoelectric sensor 13 is made, for example, by an adhesive, preferably one corresponding to the index-matching medium 20.

There may, of course, be more than one optical filter both between the light source 10 and the GRIN lens of the excitation light guide 11 and between the GRIN lens of the emission light guide 12 and the photoelectric sensor 13.

In the first embodiment, which is shown in FIG. 1, the excitation light guide 11 and the emission light guide 12 are located in receiving openings in a holding body 17, which receiving openings are inclined relative to each other. The end face 14 of the structural unit formed according to the invention by the two light guides 11, 12 ends substantially flush with one of the physical boundary surfaces of the holding body 17. It is, of course, only possible in this construction for the joining together of the two light guides 11, 12 described hereinbefore to be carried out after their insertion into the receiving openings in the holding body 17.

The mechanical part of the first embodiment of the device according to the invention comprises the sample container 2 holding the substance 3, the fluorescence changer 4, and a carrier 5 which is made, for example, of glass or plastics material. It is especially advantageous for the carrier 5 to consist of a material having a refractive index that corresponds, to within substantially +/−20%, to the refractive indices of the two light guides 11, 12, since, thereby, reflection of the excitation light at the carrier 5 is virtually avoided and hence the scattered light reaching the photoelectric sensor 13 is reduced. Deposited on the carrier 5, which, for example, has a thickness of about 100–150 μm, is the fluorescence changer 4, purely by way of example in the form of a layer of less than ~15 μm thickness. The carrier 5 together with the fluorescence changer 4 substantially forms one boundary surface of the sample container 2, in such a manner that the fluorescence changer 4 is towards the interior of the sample container 2 and therefore can be contacted by the substance 3. Purely by way of example, the sample container 2 is substantially cuboid. Inside it, the substance 3 may be either still or flowing. For the latter alternative it is, of course, necessary for the sample container 2 to have, in addition, inlet and outlet openings.

In the first embodiment of the device according to the invention, the connection is made between the mechanical part and the optical part, which comprises at least the light source 10, the light guides 11, 12 and the photoelectric sensor 13, by simply fastening the carrier 5 to the end face 14 and the holding body 17 by means of the index-matching medium 20 in such a manner that the excitation light emerging from the end face 14 meets the fluorescence changer 4 at least partially.

In the embodiment shown in FIG. 1, the structural unit of excitation light guide 11 and emission light guide 12 is in a form in which both GRIN lenses are 0.5 pitch lenses having the common focal point B which lies in the region of the fluorescence changer 4. The reason why that focal point B appears somewhat spatially separate from the fluorescence changer 4 in FIG. 1 is that the drawing is not to scale. Purely illustrative numerical values are: ~1 μm for the thickness of the index-matching medium 20; ~100 μm for the thickness of the carrier 5; ~1 μm for the thickness of the fluorescence changer 4. Those numbers show that the distance between the focal point B and the fluorescence changer 4 is practically negligible. The beam path is indicated in FIG. 1 by the light beams A1, A2 of the excitation light and by the light beams P1, P2 of the emission light. The excitation light, which comes from a point A, is focused by the GRIN lens of the excitation light guide 11 in the focal point B and excites the fluorescence of the fluorescence changer 4. At least part of the emission light coming from the point B is re-focused by the GRIN lens of the emission light guide 12 onto the point C and then passes through the second optical filter onto the photoelectric sensor 13. In that arrangement, the points A, B, C are substantially optically equivalent, as a result of which good excitation of the fluorescence, on the one hand, and efficient collection of the emission light, on the other, occurs.

The preferred embodiment of the device according to the invention shown in FIG. 1 provides the additional advantage that the concept of pigtailing is consistently implemented over the entire light path from the light source 10 to the photoelectric sensor 13. All of the optical elements are connected to one another by the index-matching medium 20 in a mechanically stable manner, so that vibrations do not interfere with the light path. Furthermore, the number of optical transitions is reduced to a minimum. As a result, other than in the region of the fluorescence changer 4, the excitation light and the emission light always propagate in media of substantially constant optical density, which reduces the scattered light caused by reflection. Since the individual optical elements have comparable thermal expansions and are in thermal contact with one another, there is also virtually no interference from thermal causes.

A number of variants of the first embodiment of the device according to the invention are described below, the following recitation not being definitive.

The connection between the optical part and the mechanical part can also be made by optically contacting the end face 14 with the carrier 5 directly, that is to say without the index-matching medium between them. This is possible, for example, by fastening the carrier 5 to the holding body 17 outside the light path. On the other hand, it is possible for the sample container 2 to be constructed in such a manner that it includes the carrier 5 together with the fluorescence changer 4, and that the walls of the sample container extend as far as the holding body 17, to which they can then be fastened. The advantages of pigtailing are not eliminated as a result of the direct contact between the end face 14 and the carrier 5, since the latter two parts are manufactured especially preferably from materials having refractive indices that correspond to within substantially +/−20%.

It is furthermore also possible for the sample container 2, the fluorescence changer 4 and the carrier 5 to be constructed in the form of a capillary tube for the substance 3. The wall of the capillary tube then assumes the function of the carrier 5 and the interior of the capillary tube the function of the sample container 2. The fluorescence changer 4 may in this case be located inside the capillary tube, for example as a layer on the inside wall, or the wall of the capillary tube is made of a material that is suitable as a fluorescence changer.

The arrangement of the excitation light guide 11 and the emission light guide 12 in FIG. 1 is purely an example. The unit consisting of the light source 10 and the excitation light guide 11 is, of course, interchangeable with the unit consisting of the photoelectric sensor 13 and the emission light guide 12. That is to say, the emission light guide 12 together with the photoelectric sensor 13 and the excitation light guide 11 together with the light source 10 may also be arranged in such a manner that the optical axis O2 of the emission light guide 12 is perpendicular to the end face 14 and the optical axis O1 of the excitation light guide 11 is at an oblique angle thereto.

Furthermore, it is also possible when manufacturing the structural unit of excitation light guide 11 and emission light guide 12 to cut off that GRIN lens which has its optical axis perpendicular to the end face 14. FIG. 2 shows the optical part of such a likewise preferred variant of the first embodiment. In that variant, the excitation light guide 11 and the emission light guide 12 are arranged in the holding body 17 in such a manner that the optical axis O2 of the emission light guide 12 is perpendicular to the end face 14 and the optical axis O1 of the excitation light guide 11 is at an oblique angle thereto. In addition, in that variant, the GRIN lens that has its optical axis perpendicular to the end face 14, namely that of the emission light guide 12, is cut off and fastened to the GRIN lens of the excitation light guide by means of the index-matching medium 20. It is, of course, necessary in that arrangement of the two light guides 11, 12 for the GRIN lens of the excitation light guide 11 also to be slanted and polished at its boundary surface facing the end face 14.

In addition, GRIN lenses of a different length may be used for the excitation light guide 11 and/or for the emission light guide 12, and the GRIN lenses of the excitation light guide 11 and the emission light guide 12 may also have different pitch values. Purely by way of example, the GRIN lens of the excitation light guide may, as drawn in FIG. 1, have the length 0.5 pitch and the GRIN lens of the emission light guide 12 may be a 0.25 pitch lens. The pencil of emission light coming from the focal point B is thereby made broader and leaves the GRIN lens of the emission light guide 12 as parallel light. As a result, the photoelectric sensor 13 is generally illuminated over a larger surface area.

FIG. 3 shows the optical part of a second preferred embodiment of the device according to the invention. There are differences from the first embodiment only in the constructions of the excitation light guide 11 and the emission light guide 12. The foregoing remarks concerning the other elements, for example the entire mechanical part, apply also to the second embodiment, it being possible especially to use the described variants and advantageous measures in this case also.

In the second embodiment, the excitation light guide 11 comprises a first GRIN lens 30, a second GRIN lens 31 and the optical filter 15. The emission light guide 12 comprises a third GRIN lens 32, a fourth GRIN lens 33 and the second optical filter 16. The four GRIN lenses 30, 31, 32, 33 are each in the form of 0.25 pitch lenses, so that both the excitation light guide 11 and the emission light guide 12 form a 0.5 pitch lens in each case.

As explained hereinbefore, the first GRIN lens 30 is optically connected to the light source 10. The planar boundary surface of the GRIN lens 30 facing away from the light source 10 is connected to the optical filter 15 and the latter is connected to the planar boundary surface of the second GRIN lens 31. Especially preferably, the connections inside the excitation light guide 11 are made by means of a transparent adhesive corresponding to the index-matching medium 20. In an analogous manner, the third 32 and the fourth GRIN lens 33 are connected to the second optical filter 16 and the emission light guide 12 is connected to the photoelectric sensor 13.

As mentioned above, either the second GRIN lens 31 of the excitation light guide 11 or the fourth GRIN lens 33 of the emission light guide 12 is cut at an oblique angle to its optical axis and the cut face is subsequently polished. The excitation light guide 11 and the emission light guide 12 are then inserted into the receiving openings in the holding body 17 and cemented together to form the structural unit by means of the index-matching medium 20. The arrangement shown in FIG. 3 is, of course, purely an example. The emission light guide 12 together with the photoelectric sensor 13 and the excitation light guide 11 together with the light source 10 may also be arranged in such a manner that the optical axis O2 of the emission light guide 12 is perpendicular to the end face 14 and the optical axis O1 of the excitation light guide 11 is at an oblique angle thereto.

Since, in the second embodiment, the optical filter 15 is located substantially in the middle of the excitation light guide 11, the first GRIN lens 30 can be placed closer to the light source 10, which results in the advantage that the light emitted by the light source 10 is used more efficiently. The excitation light coming from the point A, shown symbolically by the two light beams A1, A2, is transformed by the first GRIN lens 30 into parallel light. This means that the light beams A1, A2 emerge perpendicularly from the planar boundary surface of the first GRIN lens 30 facing the optical filter 15 and accordingly also meet the optical filter 15 perpendicularly. For that reason, no dispersion effects occur in the optical filter 15. After passing through the optical filter 15, the excitation light meets the planar boundary surface of the second GRIN lens 31 likewise perpendicularly as a parallel pencil of light, and is focused by the latter onto the focal point B. Since, between the two GRIN lenses 30, 31, the excitation light is in the form of a parallel pencil of light that propagates in the direction of the optical axis, the thickness of the optical filter 15 and whether more than one filter is located at that point are immaterial to the optical imaging properties of the excitation light guide 11.

The light path of the emission light coming from the focal point B takes an analogous course. The emission light is shown schematically in FIG. 3 by the two light beams P1, P2. The emission light likewise meets the second optical filter 16 perpendicularly as a parallel pencil of light, so that no dispersion effects occur in that filter either. The third GRIN lens 32 then focuses the emission light onto the point C which is now, in contrast to FIG. 1, directly on the photoelectric sensor 13.

FIG. 4 shows the optical part of a third preferred embodiment of the device according to the invention. There are differences from the first two embodiments only in the optical part. The foregoing remarks concerning the other elements, for example the entire mechanical part, apply also to the third embodiment, it being possible especially to use the described variants and advantageous measures analogously in this case also. In the third embodiment, the optical part comprises, in addition, a reference light guide 35 and a second photoelectric sensor 36. The reference light guide 35 comprises a material that has a refractive index gradient substantially perpendicular to the principal direction of propagation of the light in the reference light guide 35, which principal direction is determined by an optical axis O3. Especially preferably, the reference light guide 35 comprises at least one optical gradient index element, especially a GRIN lens.

The reference light guide 35 is connected to the structural unit of excitation light guide 11 and emission light guide 12 in a manner analogous to that described hereinbefore for the joining together of the said structural unit. In the embodiment shown in FIG. 4, the emission light guide 12 is so arranged that its optical axis O2 is perpendicular to the end face 14, the excitation light guide 11 is so arranged that its optical axis O1 is at an oblique angle to the end face 14 and the reference light guide 35 is so arranged that its optical axis O3 lies in the plane determined by the other two optical axes O1 and O2 and, in addition, forms with the optical axis O2 substantially the same angle as that formed between the two optical axes O1 and O2.

The connection between the reference light guide 35 and the second photoelectric sensor 36 is made, for example, by an adhesive, preferably one corresponding to the index-matching medium 20. In the embodiment shown in FIG. 4, the holding body 17 is provided with an additional receiving opening for the reference light guide 35.

The reference light guide 35 offers, together with the second photoelectric sensor 36, the additional advantage that changes in the excitation light, for example intensity fluctuations, can be detected. Part of the excitation light is reflected in the region of the fluorescence changer 4 and, by virtue of the substantially symmetrical arrangement of the reference light guide 35 and the excitation light guide 11 in relation to the emission light guide 12, passes through the reference light guide 35 onto the second photoelectric sensor 36. By comparison of the signal registered by the second photoelectric sensor 36, which serves as a reference for the excitation light, with the signal produced by the emission light in the photoelectric sensor 13, the accuracy of the actual measurement can thus be further increased.

In FIG. 5, the optical part of a fourth, likewise preferred, embodiment of the device according to the invention is shown. In that embodiment, no GRIN lens or other optical gradient index element has been provided in the emission light guide. With the exception of the second optical filter 16, the emission light guide 12 consists entirely of the index-matching medium 20, that is to say the space formed between the excitation light guide 11 and the second optical filter 16 by the receiving opening in the holding body 17 for the emission light guide 12 is bridged by the index-matching medium 20. The second optical filter is, of course, in this embodiment also, merely optional. If that filter 16 is dispensed with, the index-matching medium connects the excitation light guide 11 directly to the photoelectric sensor 13.

That fourth embodiment is preferred especially in those cases where the intensity of the emission light is sufficiently great that the optical focusing properties of the emission light guide 12 can be dispensed with, since, in comparison with the other embodiments, the one shown in FIG. 5 can be manufactured distinctly more easily from a technical point of view and also more cheaply.

The variants and measures described above, for example with regard to the construction of the mechanical part and with regard to the arrangement of the excitation light guide 11 and the emission light guide 12, can, of course, be used analogously also in the fourth embodiment. It is furthermore possible for the additional reference light guide 35 to be provided therein also.

This invention also relates to the optical detection apparatus for analytical measurement of substances, which apparatus uses a plurality, and preferably six, of the optical detection devices according to the invention. Since that apparatus also has the advantage that the mechanical part can be separated from the optical part in a simple manner, the apparatus according to the invention is suitable for a large number of applications, especially for those in which a substance, for example blood, is to be examined with regard to several constituents. The space-saving construction of the device according to the invention allows the apparatus according to the invention to be in a very compact form, as a result of which it is especially suitable for mobile use.

According to the invention, the optical detection apparatus comprises at least two optical detection devices according to the invention of the kind described hereinbefore. FIG. 6 is a schematic view in perspective of a preferred embodiment of the apparatus according to the invention, the front face being shown in section. In that embodiment, the apparatus comprises six optical detection devices. Reference numeral 40 denotes in that Figure in each case an optical unit consisting of the light source 10, the excitation light guide 11, the emission light guide 12, the index-matching medium 20 connecting the latter two, and the photoelectric sensor 13. The light guides 11, 12 may, of course, optionally comprise the optical filters 15, 16 in addition.

The optical units 40 are located especially preferably in receiving openings in the holding body 170, which receiving openings are inclined one to another in pairs. The sample containers 2 are formed by a common measurement chamber 41 for the substance 3. Purely by way of example, the measurement chamber 41 is substantially cuboid. The fluorescence changers 4 are located on a common carrier element 42 that, especially preferably, has a refractive index corresponding, to within substantially +/−20%, to the refractive indices of the light guides 11, 12. The carrier element 42 together with the fluorescence changers 4 substantially forms one of the boundary surfaces of the measurement chamber 41, in such a manner that the fluorescence changers are towards the interior of the measurement chamber 41 and accordingly can be contacted by the substance 3.

FIG. 7 shows, purely by way of example, a possible way of constructing the carrier element 42 together with the fluorescence changers 4. The various fluorescence changers 4 are deposited on the carrier element 42 in the form of layers having a thickness of, for example, less than ~15 μm. The rectangular shape shown in FIG. 7 is, of course, purely an example. The fluorescence changers 4 may also have a substantially round shape. It is possible, for example, to deposit the various fluorescence changers 4 directly on the carrier element 42. In another variant, each of the fluorescence changers 4 is first placed on one of the carriers 5 and, once in a suitable form, the various carriers 5 together with the fluorescence changers 4 are connected to one another and thus substantially form the carrier element 42.

In FIG. 6, the mechanical part of the apparatus according to the invention, which comprises at least the measurement chamber 41 for the substance 3 and the carrier element 42 together with the fluorescence changers 4, is connected to the optical part, which comprises the optical units 40 in the holding body 170, by the index-matching medium 20. The connection is made in such a manner that the various optical units 40 are each associated with exactly one fluorescence changer 4. This means that, as shown schematically in FIG. 7, each of the fluorescence changers 4 is optically connected to one of the end faces 14 of the light guides 11, 12. This has the advantage that each of the fluorescence changers 4 is met substantially only by that excitation light which emerges from the end face 14 of the optical unit 40 associated with it, and that the emission light emitted by that same fluorescence changer meets substantially only the photoelectric sensor 13 of the associated optical unit 40. A further advantage is that the various fluorescence changers 4 can be sensitive to various constituents of the substance 3. The substance 3 can therefore be examined with regard to several constituents in one measurement operation.

The various embodiments, advantageous measures and variants described in the foregoing for the optical detection device according to the invention may, of course, be used in corresponding manner also for the optical detection apparatus.

For example, the substance 3 may be in still or flowing form in the measurement chamber 41.

It is also possible, for example, to connect the optical and mechanical parts of the apparatus according to the invention to each other directly, that is to say without the index-matching medium 20. This can be done in a manner analogous to that described in the foregoing for the detection device.

Similarly analogously to the detection device, the measurement chamber 41 and the carrier element 42 together with the fluorescence changers 4 may be in the form of a capillary tube for the substance 3, for example such that different substantially spatially separate regions of the capillary tube with the fluorescence changers 4 are sensitive to different constituents of the substance 3.

Furthermore, a reference light guide with a further photoelectric sensor, corresponding to the elements identified by reference numerals 35 and 36 in FIG. 4, may additionally be provided in at least one of the optical units 40. In that manner, a reference signal with which changes in the excitation light can be detected can be registered also with the optical detection apparatus.

Alternatively, however, it is also possible to use one of the optical units shown in FIG. 6 for the production of the reference signal, in place of the additional reference light guide. In that embodiment, five of the optical units 40 are then used for the analytical measurement of the substance and one of the optical units 40 is used for the production of the reference signal. Since, as a rule, all the light sources 10 are powered by the same voltage source, it is possible to detect with such an arrangement, for example, fluctuations in the intensity of the excitation light.

The invention further relates to the optical analysis apparatus for fluorescence measurements of a substance. The analysis apparatus comprises a measuring device 50 for carrying out the fluorescence measurement, an electronic power supply and control unit 90 which supplies the measuring device 50 with current, electronic amplification and evaluation means 80 which process the signals supplied by the measuring device, and a temperature measuring and regulating device 70 which controls and stabilises at least the temperature of the substance 3 in the measuring device 50. According to the invention, the measuring device 50 is an optical detection apparatus or an optical detection device of the kind to which the invention relates and that is described hereinbefore.

A preferred form of construction of the analysis apparatus according to the invention is shown schematicaly in FIG. 8. The measuring device 50 comprises the optical detection apparatus with six optical units 40 in which the light sources 10 are LEDs. The electronic power supply and control unit 90 comprises a stabilised voltage source which supplies the LEDs with current. The electronic amplification and evaluation means 80 receive the signals from the photoelectric sensors 13, further process them, for example by means of an amplifier, and supply them for ultimate evaluation. The ultimate evaluation, display or printing-out of the measurement results can then be carried out by means of an electronic data-processing system 100, which may also be used to control the entire measuring process and, for example, to store the data.

In that embodiment, the temperature is controlled by means of the fact that the measuring device 50 is held in a housing consisting of a material having good thermal conductivity, it being possible to influence and stabilised the temperature of the housing, and therewith that of the measuring device 50 with the substance 3 present in it, by way of a Peltier element 60. The Peltier element 60 is supplied with power and controlled by the temperature measuring and regulating device 70. The substance 3 can accordingly be examined at a desired stabilisable temperature.

The analysis apparatus according to the invention accordingly has the advantages of the detection device according to the invention and of the detection apparatus according to the invention. The analysis apparatus has especially the advantage that the mechanical part of the measuring device can be replaced in a simple manner without further manipulation of the optical part of the measuring device being necessary. As a result, the optical part, which can be used repeatedly, can be of a higher quality and the mechanical part can be designed to be used only once. For that reason, the analysis apparatus according to the invention can be manufactured economically, is very flexible with regard to its use and is suitable for a large number of applications also outside modern analysis and research laboratories. The mechanically stable construction of the optical part makes the analysis apparatus robust and insensitive to shocks and vibrations. Coupled with its simple handling, the analysis apparatus according to the invention is therefore especially suitable for mobile use also.

What is claimed is:

1. An optical detection device for analytical measurements of a substance, comprising a sample container for the substance, a fluorescence changer, a light source for emitting an excitation light, a photoelectric sensor for sensing an emission light coming from the fluorescence changer, an excitation light guide which substantially guides the excitation light emitted by the light source in such a manner that it meets at least part of the fluorescence changer, and an emission light guide which substantially guides the light emitted by the fluorescence changer in such a manner that it meets the photoelectric sensor, at least the excitation light guide comprising a material that has a refractive index gradient substantially perpendicular to the principal direction of propagation of the light in the light guide, wherein the excitation light guide is connected to the emission light guide in such a manner that the two light guides substantially form a structural unit having an end face facing the fluorescence changer, the end face physically corresponding substantially to a boundary surface of one of the two light guides, and the end face substantially forming both an optical emergence surface for the light passing from the light source through the excitation light guide and an optical entry surface for the emission light coming from the fluorescence changer.

2. A device according to claim 1, wherein the emission light guide and the excitation light guide are cemented together by means of an index-matching medium.

3. A device according to claim 1, wherein the emission light guide and the excitation light guide are inclined relative to each other in such a manner that the principal directions of propagation of the light in the two light guides, determined by optical axes, are at an oblique angle to each other.

4. A device according to claim 1, wherein the fluorescence changer is located on a carrier having a refractive index that corresponds, to within substantially +/−20%, to the refractive indices of the two light guides, and the carrier is optically connected to the end face of the two light guides.

5. A device according to claim 1, wherein a nodal line of the structural unit formed by the excitation light guide and the emission light guide lies substantially in the region of the fluorescence changer.

6. A device according to claim 1, wherein the excitation light guide and/or the emission light guide contain at least one optical gradient index element.

7. A device according to claim 1, wherein the excitation light guide comprises at least one optical filter for selecting the wavelength range of the excitation light.

8. A device according to claim 1, wherein the emission light guide comprises at least a an optical filter for selecting the wavelength range of the light meeting the photoelectric sensor.

9. A device according to claim 1, wherein the light source is a light-emitting diode that radiates coherent or incoherent light.

10. A device according to claim 1, wherein the excitation light guide and the emission light guide are located in receiving openings in a holding body, which receiving openings are inclined one to another.

11. A device according to claim 1, wherein the emission light guide is substantially made from an index-matching medium, and optionally includes an optical filter.

12. A device according to claim 1, wherein a reference light guide having an optical axis is additionally provided which is connected to the structural unit, in such manner that the optical axes of the three light guides lie in one plane and two of the optical axes form with the third substantially the same angle, and wherein, in addition, a second photoelectric sensor is provided at a planar boundary surface of the reference light guide facing away from the end face of the structural unit.

13. An optical detection apparatus for the analytical measurement of substances, which comprises at least two optical detection devices each constructed in accordance with any one of the preceding claims.

14. An apparatus according to claim 13, wherein at least all the excitation light guides and emission light guides are located in receiving openings in a holding body, which receiving openings are inclined one to another in pairs.

15. An apparatus according to claim 13, wherein all the sample containers are formed by a common measurement chamber.

16. An apparatus according to claim 13, wherein the fluorescence changers are located on a common carrier element, the carrier element having a refractive index that corresponds, to within substantially +/−20%, to the refractive indices of the light guides and wherein the said carrier element is connected to the end faces of the light guides.

17. An apparatus according to claim 13, wherein each of the excitation/emission light guides is associated with a respective fluorescence changer which is met substantially only by the excitation light from the excitation light guide associated with it.

18. An apparatus according to claim 13, wherein the fluorescence changers are sensitive to various constituents of the substance.

19. An optical analysis apparatus for fluorescence measurements of a substance, comprising a measuring device for fluorescence examinations, an electronic power supply and control unit which provides current for the measuring device, electronic amplification and evaluation means which process signals supplied by the measuring device, and a temperature measuring and regulating device for controlling and stabilizing temperature, wherein the measuring device comprises an optical detection apparatus according to claim 13.

* * * * *